United States Patent [19]

Lampel et al.

[11] Patent Number: 5,041,372

[45] Date of Patent: Aug. 20, 1991

[54] PROBE TO IDENTIFY ENTEROINVASIVE *E. COLI* AND SHIGELLA SPECIES

[75] Inventors: Keith A. Lampel, Germantown, Md.; James A. Jagow, Arlington, Va.

[73] Assignee: The United States of America as represented by the Department of Health and Human Services, Washington, D.C.

[21] Appl. No.: 266,038

[22] Filed: Nov. 2, 1988

[51] Int. Cl.$^5$ .......................... C12Q 1/68; C12Q 1/24; G01N 33/566; C07H 15/12
[52] U.S. Cl. ......................................... 435/6; 435/243; 435/259; 435/29; 435/34; 536/26; 536/27; 536/28; 436/501
[58] Field of Search ................. 536/27, 28, 26; 435/6, 435/243, 259, 849, 29, 34; 935/77, 78; 436/501

[56] References Cited

U.S. PATENT DOCUMENTS 4,816,389  3/1989  Sansonetti et al. ..................... 435/6

OTHER PUBLICATIONS

Sakai et al., Infect. Immun. 54(2): 395–402 (Nov., 1986).

*Primary Examiner*—Robert A. Wax
*Assistant Examiner*—Stephanie W. Zitomer
*Attorney, Agent, or Firm*—Glenna Hendricks

[57] ABSTRACT

The invention provides a method for preparation of probes for use in detecting enteroinvasive *Escherichia coli* and Shigella species. The small probes provide reliable and inexpensive means for detecting the pathogens in food samples and in environmental and clinical samples.

9 Claims, 4 Drawing Sheets

Strains
354 270

PROBE TO IDENTIFY ENTEROINVASIVE E. COLI AND SHIGELLA SPECIES

The invention described herein provides a method for preparation of probes for use in detecting enteroinvasive *Escherichia coli* and Shigellae species. The small probes of the invention provide reliable and inexpensive means for detecting such pathogens in food samples and in environmental and clinical samples.

BACKGROUND OF THE INVENTION

Invasive strains of Shigella and enteroinvasive *E. coli* have been shown to carry a plasmid (the invasiveness plasmid) that encodes genes necessary for virulence. (Hale, et al., *Infect. Immun.* 40: 340–350 (1983)) Based on identification of critical regions on this plasmid, DNA probes have been developed that identify potentially invasive isolates (Boileau, et al., *J. Clin. Microbiol.* 20:(1984) Small and Falkow (In L. Leive (ed.), Microbiology-1986. American Society for Microbiology, Washington, D.C., pp. 121-124) had described a 2.5 kilobase HindIII fragment of the invasiveness plasmid from an enteroinvasive *E. coli* strain for use in testing invasivness of the enteric organisms. Previously, it had been demonstrated that virulence of these organisms could be predicted by inoculating the conjunctival sac of a guinea pig with a strain of Shigella. Invasive strains produced a purulent keratoconjunctivitis associated with invasion of corneal epitheial cells and infiltration with polymorphonuclear leukocytes similar to that seen in intestinal lesions caused by Shigellae.

The use of guinea pigs in the identification of pathogenic organisms in the food supply and in clinical speciments is clearly expensive and time-consuming. The use of large fragments such as the 17-kilobase EcoRI fragment of Boileau and the 2.5-kilobase HindIII fragment of Small and Falkow are expensive to make and use.

DESCRIPTION OF THE FIGURES

A partial restriction map of the 2.5 kilobase pair HindIII fragment is shown. Restriction sites HindIII (H), PstI (P), and DraI (D) are marked. The box below the map is the 627 base pair open reading frame (ORF) and the box above is the sequence used to synthesize an oligonucleotide for probe analysis. Arrows indicate the direction and length of sequence generated by the Sanger dideoxynucleotide chain termination method. For double-stranded sequencing, plasmid templates are generated by the Erase-a-base system of Promega.

Total RNA from an invasive *Shigella flexneri* strain (270) and an avirulent strain (354) were hybridized against a 2.0 kilobase pair HindIII/PstI fragment. Two transcripts of 700 and 500 bases were detected as indicated by the arrows.

The 230 kilobase pair plasmid was isolated from *Shigella flexneri* 270, digested with HindIII, BamHI, and EcoRI, run on an agarose gel, transferred to nitrocellulose filter paper, and hybridized with the 2.5 kilobase pair HindIII fragment from *E. coli*. As seen in the Southern blots, the 2.5 kilobase pair from the large plasmid in enteroinvasive *E. coli* hybridized with a 2.5 kilobase pair HindIII fragment and >20 kilobase pair EcoRI and BamHI fragments from the plasmid isolated from *Shigella flexneri*. Sequence data from the 2.5 kilobase pair HindIII fragment from *Shigella flexneri* is identical with its counter part from *E. coli*.

To confirm that the Shigella probe was specific for the 230-kilobase pair plasmid that is associated with Sereny-positive Shigellae and *E. coli* organisms, plasmid DNA was isolated from several of the strains tested as shown in Table 1 and hybridized with the *Shigella* probe. Only Sereny-positive strains hybridized with the probe. Lanes marked 1–5 are *E. coli*. Lanes 6, 10, and 24 are *Sh. flexneri*, lanes 7, 11, 12,14, and 15 are *Sh. sonnei*. lane 9 is *Sh. dysenteriae*, and lane 8 is a Sh. species.

DETAILED DESCRIPTION OF THE INVENTION

Figure 1:
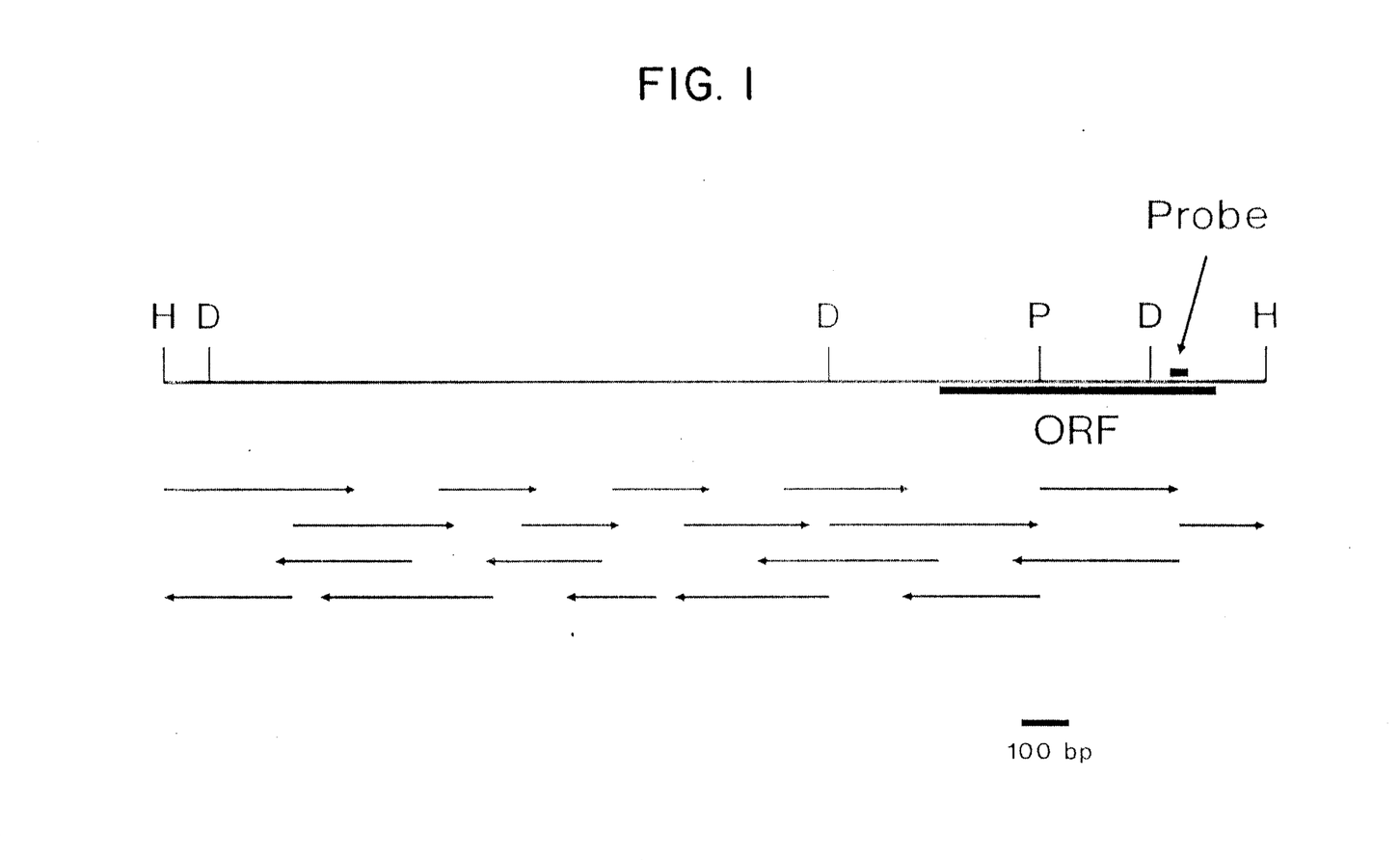
FIG. 1: Sequencing Strategy
Figure 2:
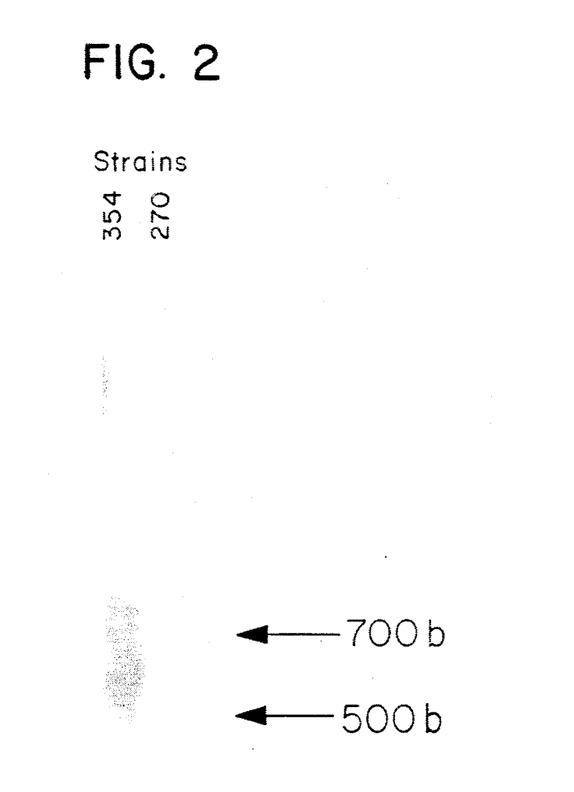
FIG. 2. Northern Hybridization Blots
Figure 3:
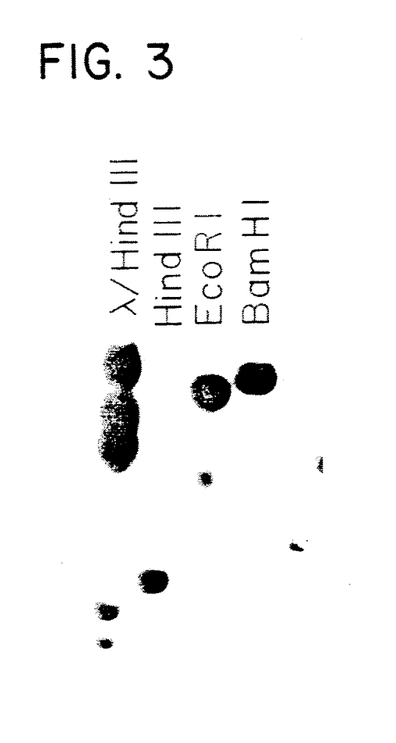
FIG. 3. Southern Hybridization Blots
Figure 4:
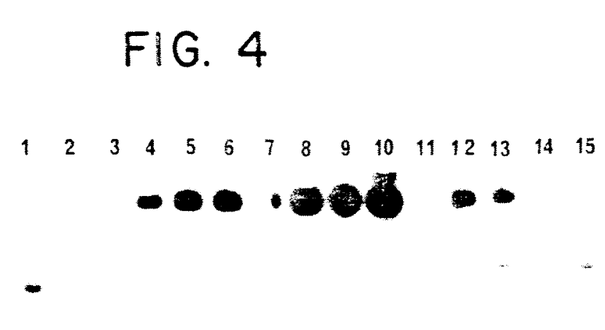
FIG. 4. Southern Blots of *Shigella* and *E. coli* Hybridized with Shigella probes.

The 2.5-kilobase fragment of Small and Falkow has now been sequenced and has been found to have the described sequence of bases. An open reading frame (ORF) is seen beginning at position 108 to 738. The peptide sequence encoded by the open reading frame is indicated below the base sequence of this peptide. The presence of this reading frame has been supported by Northern blotting. It has now been found that probes consisting of oligoneoxyribonucleotides complementary to a specific sequence in this open reading frame can be used to detect enteroinvasive *E. coli* and Shigella species in foods and from environmental and clinical isolates. Such probes must be at least 18 bases long and should, ideally, encompass one of the more diverse portions of complementary strand. In no case should a sequence employed as a probe have more than four consecutive identical bases. It is preferred that no more than two consecutive bases be identical. A preferred sequence tested in this laboratory is the sequence 5'-TAATACTCCTGAACGGCG-3'. Probes of such length can easily be made by known means in a nucleotide sythesizer.

The synthetic DNA probe may be used in nucleic acid hybridizations either using lysed bacteria on a solid support (e.g. filter papers or nitrocellulose or nylon membranes) or using total fractionated nucleic acid isolated from bacteria which is transferred to a solid support. The probe so designed specifically detects enteroinvasive *E. coli*, and Shigella species, including *Sh. flexneri, Sh. sonnei, Sh. dysenteria* and *Sh. boydii*. Nucleic acid hybridizations entail use of a radioactively or non-radioactively labelled DNA (probe) which binds to a complementary strand of DNA or RNA in the target. (e.g. nucleic acid from lysed bacterial cells or isolated nucleic acid.)

The use of the probes described herein have two advantages over the current technology: 1) The probes discriminate between virulent and non-virulent enteroinvasive *E. coli* and Shigella species which classical microbiological techniques are not able to distinguish. 2) Since the sequences of the oligodeoxyribonucleotides are known, they are not only more stable, but are also easier and less expensive to make and distribute than the 17 and 2.5 kilobase pair fragments previously known.

The 2.5-kilobase fragment received from Small and Falkow was found to have the following sequence:

| | | | | | | | | | | | | | | | | | | | | |
|---|---|---|---|---|---|---|---|---|---|---|---|---|---|---|---|---|---|---|---|---|
| 1 | AA<br>--<br>TT | GCT<br>---<br>CGA | TAT<br>---<br>ATA | AGG<br>-+-<br>TCC | TGT<br>---<br>ACA | CTC<br>---<br>GAG | AAT<br>-+-<br>TTA | ATC<br>---<br>TAG | TTT<br>---<br>AAA | GCT<br>---<br>CGA | ACT<br>-+-<br>TGA | TCT<br>---<br>AGA | TTC<br>---<br>AAG | TGG<br>-+-<br>ACC | ATG<br>---<br>TAC | GTA<br>---<br>CAT | TGA<br>---<br>ACT | GGT<br>-+-<br>CCA | TTT<br>---<br>AAA | A<br>+<br>T |
| | | | | | | | | | | | | | | | | | | | | 60 |
| 61 | TT<br>--<br>AA | GTC<br>---<br>CAG | TTT<br>---<br>AAA | TTA<br>---<br>AAT | GAA<br>-+-<br>CTT<br>Glu | AGT<br>---<br>TCA<br>Ser | TGA<br>---<br>ACT | AAT<br>---<br>TTA | GTT<br>---<br>CAA | GCT<br>---<br>CGA | ACT<br>-+-<br>TGA | TTC<br>---<br>AAG | TGG<br>-+-<br>ACC<br>Trp | AAC<br>---<br>TTG<br>Asn | ATG<br>---<br>TAC<br>Met | CAT<br>---<br>GTA<br>His | GTA<br>---<br>CAT | TGG<br>---<br>ACC | ATT<br>---<br>TAA | TCA<br>---<br>AGT<br>Ser | A<br>+<br>T |
| | er | Trp | Phe | Leu | | | | | | | | | | | | | | | | | 120 |
| 121 | CT<br>--<br>GA<br>la | CCA<br>---<br>GGT<br>Pro | TTA<br>---<br>AAT<br>Leu | AAT<br>---<br>TTA<br>Asn | GAA<br>-+-<br>CTT<br>Glu | AGT<br>---<br>TCA<br>Ser | ATT<br>---<br>TAA<br>Ile | CAT<br>-+-<br>GTA<br>His | CCA<br>---<br>GGT<br>Pro | TTT<br>---<br>AAA<br>Phe | TTT<br>---<br>AAA<br>Phe | CTC<br>-+-<br>GAG<br>Leu | AAC<br>---<br>TTG<br>Asn | TGG<br>-+-<br>ACC<br>Trp | GGT<br>---<br>CCA<br>Gly | TTG<br>---<br>AAC<br>Leu | GAC<br>---<br>CTG<br>Asp | ATT<br>---<br>TAA<br>Ile | TCA<br>---<br>AGT<br>Ser | A<br>+<br>T<br>T<br>S |
| | | | | | | | | | | | | | | | | | | | | 180 |
| 181 | TA<br>--<br>AT<br>le | CCT<br>---<br>GGA<br>Pro | GTG<br>---<br>CAC<br>Val | ATT<br>---<br>TAA<br>Ile | TTT<br>---<br>AAA<br>Phe | TTT<br>---<br>AAA<br>Phe | AAT<br>---<br>TTA<br>Asn | TTA<br>-+-<br>AAT<br>Leu | GCA<br>---<br>CGT<br>Ala | TCA<br>---<br>AGT<br>Ser | TTT<br>---<br>AAA<br>Phe | GGT<br>-+-<br>CCA<br>Gly | ACT<br>---<br>TGA<br>Thr | AAG<br>-+-<br>TTC<br>Lys | TCT<br>---<br>AGA<br>Ser | AAG<br>---<br>TTC<br>Lys | TTT<br>---<br>AAA<br>Phe | AGA<br>---<br>TCT<br>Arg | TCT<br>---<br>AGA<br>Ser | G<br>+<br>C<br>A |
| | | | | | | | | | | | | | | | | | | | | 240 |
| 241 | CT<br>--<br>GA<br>er | GTT<br>---<br>CAA<br>Val | TTT<br>---<br>AAA<br>Phe | CGT<br>---<br>GCA<br>Arg | TGC<br>-+-<br>ACG<br>Cys | CAT<br>---<br>GTA<br>His | TCT<br>---<br>AGA<br>Ser | ATT<br>---<br>TAA<br>Ile | GAA<br>-+-<br>CTT<br>Glu | CTT<br>---<br>GAA<br>Leu | TGG<br>---<br>ACC<br>Trp | CTT<br>-+-<br>GAA<br>Leu | ATG<br>---<br>TAC<br>Met | TTC<br>-+-<br>AAG<br>Phe | CAT<br>---<br>GTA<br>His | GTT<br>---<br>CAA<br>Val | GAC<br>---<br>CTG<br>Asp | ATA<br>---<br>TAT<br>Ile | GTT<br>---<br>CAA<br>Val | T<br>+<br>A<br>I |
| | | | | | | | | | | | | | | | | | | | | 300 |
| 301 | TC<br>--<br>AG<br>er | TCT<br>---<br>AGA<br>Ser | TTT<br>---<br>AAA<br>Phe | TGC<br>---<br>ACG<br>Cys | GGG<br>-+-<br>CCC<br>Gly | CTT<br>---<br>GAA<br>Leu | ACG<br>---<br>TGC<br>Thr | TTC<br>-+-<br>AAG<br>Phe | TCT<br>---<br>AGA<br>Ser | AGT<br>---<br>TCA<br>Ser | TTC<br>---<br>AAG<br>Phe | CTT<br>-+-<br>GAA<br>Leu | ATT<br>---<br>TAA<br>Ile | AAG<br>-+-<br>TTC<br>Lys | ATT<br>---<br>TAA<br>Ile | GGT<br>---<br>CCA<br>Gly | GAC<br>---<br>CTG<br>Asp | ATA<br>---<br>TAT<br>Ile | TCT<br>---<br>AGA<br>Ser | T<br>+<br>A<br>+<br>A<br>S |
| | | | | | | | | | | | | | | | | | | | | 360 |
| 361 | TC<br>--<br>AG<br>Ser | TCT<br>---<br>AGA<br>Ser | TGC<br>---<br>ACG<br>Cys | CGT<br>---<br>GCA<br>Arg | AAA<br>-+-<br>TTT<br>Lys | GAA<br>---<br>CTT<br>Glu | ACG<br>---<br>TGC<br>Thr | GAT<br>---<br>CTA<br>Asp | TGG<br>-+-<br>ACC<br>Trp | CTT<br>---<br>GAA<br>Leu | GAT<br>---<br>CTA<br>Asp | GCT<br>-+-<br>CGA<br>Ala | GCC<br>---<br>CGG<br>Ala | AGC<br>-+-<br>TCG<br>Ser | ATT<br>---<br>TAA<br>Ile | AAT<br>---<br>TTA<br>Asn | ATT<br>---<br>TAA<br>Ile | ACG<br>---<br>TGC<br>Thr | GGA<br>---<br>CCT<br>Gly | C<br>+<br>G<br>L |
| | | | | | | | | | | | | | | | | | | | | 420 |
| 421 | AC<br>--<br>TG<br>sn | CAG<br>---<br>GTC<br>Gln | TTG<br>---<br>AAC<br>Leu | GCA<br>---<br>CGT<br>Ala | TCA<br>-+-<br>AGT<br>Ser | ACG<br>---<br>TGC<br>Thr | TTC<br>---<br>AAG<br>Phe | GCA<br>-+-<br>CGT<br>Ala | TGG<br>---<br>ACC<br>Trp | TCT<br>---<br>AGA<br>Ser | TTT<br>---<br>AAA<br>Phe | GCA<br>-+-<br>CGT<br>Ala | GTA<br>---<br>CAT<br>Val | TCG<br>-+-<br>AGC<br>Ser | GTT<br>---<br>CAA<br>Val | GAT<br>---<br>CTA<br>Asp | ATT<br>---<br>TAA<br>Ile | ACG<br>---<br>TGC<br>Thr | TCT<br>---<br>AGA<br>Ser | G<br>+<br>C<br>G |
| | | | | | | | | | | | | | | | | | | | | 480 |
| 481 | AG<br>--<br>TC<br>lu | TTG<br>---<br>AAC<br>Leu | AAA<br>---<br>TTT<br>Lys | GCA<br>---<br>CGT<br>Ala | TCC<br>-+-<br>AGG<br>Ser | AAT<br>---<br>TTA<br>Asn | GAT<br>---<br>CTA<br>Asp | GCA<br>-+-<br>CGT<br>Ala | AAT<br>---<br>TTA<br>Asn | CAA<br>---<br>GTT<br>Gln | TTG<br>---<br>AAC<br>Leu | TGC<br>-+-<br>ACG<br>Cys | GCC<br>---<br>CGG<br>Ala | TCA<br>-+-<br>AGT<br>Ser | TAC<br>---<br>ATG<br>Tyr | AGT<br>---<br>TCA<br>Ser | GGT<br>---<br>CCA<br>Gly | GGA<br>---<br>CCT<br>Gly | ATG<br>---<br>TAC<br>Met | G<br>+<br>C<br>V |
| | | | | | | | | | | | | | | | | | | | | 540 |
| 541 | TC<br>--<br>AG<br>al | TTT<br>---<br>AAA<br>Phe | ATT<br>---<br>TAA<br>Ile | TTA<br>---<br>AAT<br>Leu | GAA<br>-+-<br>CTT<br>Glu | TCC<br>---<br>AGG<br>Ser | CAA<br>---<br>GTT<br>Gln | CAA<br>-+-<br>GTT<br>Gln | TTT<br>---<br>AAA<br>Phe | CAA<br>---<br>GTT<br>Gln | TTA<br>---<br>AAT<br>Leu | TAT<br>-+-<br>ATA<br>Tyr | GAT<br>---<br>CTA<br>Asp | CCG<br>-+-<br>GGC<br>Pro | TTA<br>---<br>AAT<br>Leu | AGT<br>---<br>TCA<br>Ser | CTT<br>---<br>GAA<br>Leu | ATT<br>---<br>TAA<br>Ile | TGT<br>---<br>ACA<br>Cys | T<br>+<br>A<br>S |
| | | | | | | | | | | | | | | | | | | | | 600 |
| 601 | CT<br>--<br>GA<br>er | TTC<br>---<br>AAG<br>Phe | CGT<br>---<br>GCA<br>Arg | TCA<br>---<br>AGT<br>Ser | TTA<br>-+-<br>AAT<br>Asn | AAT<br>---<br>TTA<br>Ile | ACA<br>---<br>TGT<br>Thr | TTG<br>-+-<br>AAC<br>Leu | AGT<br>---<br>TCA<br>Ser | TCT<br>---<br>AGA<br>Ser | TTT<br>---<br>AAA<br>Phe | CTG<br>-+-<br>GAC<br>Leu | ATA<br>---<br>TAT<br>Tyr | CAG<br>-+-<br>GTC<br>Gln | GTT<br>---<br>CAA<br>Val | GTT<br>---<br>CAA<br>Val | TCT<br>---<br>AGA<br>Ser | CAA<br>---<br>GTT<br>Gln | ATT<br>---<br>TAA<br>Ile | T<br>+<br>A<br>L |
| | | | | | | | | | | | | | | | | | | | | 660 |

-continued

| | | | | | | | | | | | | | | | | | | | | |
|---|---|---|---|---|---|---|---|---|---|---|---|---|---|---|---|---|---|---|---|---|
| 661 | TA<br>--<br>AT<br>eu | GCC<br>---<br>CGG<br>Ala | AGT<br>---<br>TCA<br>Ser | CCT<br>-+-<br>GGA<br>Pro | GTT<br>---<br>CAA<br>Val | ATG<br>---<br>TAC<br>Met | ATA<br>-+-<br>TAT<br>Ile | GTA<br>---<br>CAT<br>Val | TTG<br>---<br>AAC<br>Leu | TTA<br>---<br>AAT<br>Leu | CTA<br>-+-<br>GAT<br>Leu | TCA<br>---<br>AGT<br>Ser | GAA<br>---<br>CTT<br>Glu | GTA<br>-+-<br>CAT<br>Val | TTA<br>---<br>AAT<br>Leu | CTT<br>---<br>GAA<br>Leu | GGT<br>-+-<br>CCA<br>Gly | GTA<br>---<br>CAT<br>Val | TTA<br>---<br>AAT<br>Leu | TCG<br>---<br>AGC<br>Ser | A<br>+<br>T<br>720 |
| 721 | GA<br>--<br>CT<br>rg | TTG<br>---<br>AAC<br>Leu | CTC<br>---<br>GAG<br>Leu | CGC<br>-+-<br>GCG<br>Arg | AGA<br>---<br>TCT<br>Arg | TGA<br>---<br>ACT | ATG<br>-+-<br>TAC | TGA<br>---<br>ACT | TTT<br>---<br>AAA | CCG<br>---<br>GGC | TAT<br>-+-<br>ATA | CAT<br>---<br>GTA | TAC<br>---<br>ATG | TAT<br>-+-<br>ATA | TAA<br>---<br>ATT | AAG<br>---<br>TTC | TTT<br>-+-<br>AAA | ACT<br>---<br>TGA | TGC<br>---<br>ACG | AAT<br>---<br>TTA | A<br>+<br>T<br>780 |
| 781 | TT<br>--<br>AA | TAT<br>---<br>ATA | TAT<br>---<br>ATA | TTT<br>-+-<br>AAA | CAT<br>---<br>GTA | TTT<br>---<br>AAA | AAA<br>-+-<br>TTT | TCT<br>---<br>AGA | TAC<br>---<br>ATG | ATT<br>---<br>TAA | TTA<br>-+-<br>AAT | CAT<br>---<br>GTA | ATA<br>---<br>TAT | TAT<br>-+-<br>ATA | TAA<br>---<br>ATT | CTT<br>---<br>GAA | ATT<br>-+-<br>TAA | TTT<br>---<br>AAA | AAA<br>---<br>TTT | CGG<br>---<br>GCC | T<br>+<br>A<br>840 |
| 841 | GA<br>--<br>CT | ACA<br>---<br>TGT | TAA<br>---<br>ATT | ATT<br>-+-<br>TAA | TTT<br>---<br>AAA | CAC<br>---<br>GTG | AAA<br>-+-<br>TTT | TAG<br>---<br>ATC | TGT<br>---<br>ACA | ATT<br>---<br>TAA | TGT<br>-+-<br>ACA | ATA<br>---<br>TAT | TAG<br>---<br>ATC | AGG<br>-+-<br>TCC | ACA<br>---<br>TGT | GGC<br>---<br>CCG | ATC<br>-+-<br>TAG | TAA<br>---<br>ATT | AAC<br>---<br>TTG | AGA<br>---<br>TCT | A<br>+<br>T<br>900 |
| 901 | AA<br>--<br>TT | GCC<br>---<br>CGG | GAC<br>---<br>CTG | ACC<br>-+-<br>TGG | TAA<br>---<br>ATT | AAA<br>---<br>TTT | ACT<br>-+-<br>TGA | TGC<br>---<br>ACG | CGC<br>---<br>GCG | GGA<br>---<br>CCT | CGC<br>-+-<br>GCG | TAG<br>---<br>ATC | AAA<br>---<br>TTT | TAC<br>-+-<br>ATG | ACA<br>---<br>TGT | GTC<br>---<br>CAG | ATT<br>-+-<br>TAA | TAA<br>---<br>ATT | ATT<br>---<br>TAA | AGA<br>---<br>TCT | A<br>+<br>T<br>960 |
| 961 | GA<br>--<br>CT | TTT<br>---<br>AAA | AAC<br>---<br>TTG | GAT<br>-+-<br>CTA | TTT<br>---<br>AAA | GGC<br>---<br>CCG | CTT<br>-+-<br>GAA | AAT<br>---<br>TTA | GCC<br>---<br>CGG | GTT<br>---<br>CAA | AGG<br>-+-<br>TCC | GAC<br>---<br>CTG | ATT<br>---<br>TAA | TAC<br>-+-<br>ATG | TAT<br>---<br>ATA | ATC<br>---<br>TAG | ATC<br>-+-<br>TAG | CTT<br>---<br>GAA | TTC<br>---<br>AAG | TTC<br>---<br>AAG | C<br>+<br>G<br>1020 |
| 1021 | TT<br>--<br>AA | AAG<br>---<br>TTC | TGA<br>---<br>ACT | TGT<br>-+-<br>ACA | AAT<br>---<br>TTA | GCT<br>---<br>CGA | CTT<br>-+-<br>GAA | ATA<br>---<br>TAT | CAG<br>---<br>GTC | ATT<br>---<br>TAA | TGT<br>-+-<br>ACA | AAT<br>---<br>TTA | AAT<br>---<br>TTA | TAC<br>-+-<br>ATG | TGA<br>---<br>ACT | CTT<br>---<br>GAA | CGA<br>-+-<br>GCT | AAT<br>---<br>TTA | CTT<br>---<br>GAA | TGA<br>---<br>ACT | G<br>+<br>C<br>1080 |
| 1081 | GG<br>--<br>CC | TAA<br>---<br>ATT | ATA<br>---<br>TAT | CTT<br>-+-<br>GAA | TTT<br>---<br>AAA | TGC<br>---<br>ACG | TTT<br>-+-<br>AAA | TAA<br>---<br>ATT | TTC<br>---<br>AAG | TCT<br>---<br>AGA | CTT<br>-+-<br>GAA | AAA<br>---<br>TTT | TGG<br>---<br>ACC | GAT<br>-+-<br>CTA | AAT<br>---<br>TTA | CTT<br>---<br>GAA | CTT<br>-+-<br>GAA | TAA<br>---<br>ATT | CCC<br>---<br>GGG | TTT<br>---<br>AAA | T<br>+<br>A<br>1140 |
| 1141 | TT<br>--<br>AA | CTG<br>---<br>GAC | TGT<br>---<br>ACA | TCT<br>-+-<br>AGA | AAT<br>---<br>TTA | GGC<br>---<br>CCG | CCC<br>-+-<br>GGG | AAC<br>---<br>TTG | CAG<br>---<br>GTC | GCC<br>---<br>CGG | ATT<br>-+-<br>TAA | TTT<br>---<br>AAA | GTT<br>---<br>CAA | CAA<br>-+-<br>GTT | AAA<br>---<br>TTT | TGT<br>---<br>ACA | ATC<br>-+-<br>TAG | CTT<br>---<br>GAA | TGC<br>---<br>ACG | TTC<br>---<br>AAG | T<br>+<br>A<br>1200 |
| 1201 | AA<br>--<br>TT | AGC<br>---<br>TCG | TAT<br>---<br>ATA | GAC<br>-+-<br>CTG | AAT<br>---<br>TTA | TTC<br>---<br>AAG | AGA<br>-+-<br>TCT | GCC<br>---<br>CGG | TTT<br>---<br>AAA | ATT<br>---<br>TAA | AAA<br>-+-<br>TTT | TCA<br>---<br>AGT | ATT<br>---<br>TAA | GAT<br>-+-<br>CTA | AGG<br>---<br>TCC | TGA<br>---<br>ACT | TGT<br>-+-<br>ACA | CTT<br>---<br>GAA | AAT<br>---<br>TTA | TTA<br>---<br>AAT | T<br>+<br>A<br>1260 |
| 1261 | AG<br>--<br>TC | TAT<br>---<br>ATA | AAA<br>---<br>TTT | GAC<br>-+-<br>CTG | CAA<br>---<br>GTT | TTT<br>---<br>AAA | TTC<br>-+-<br>AAG | AAT<br>---<br>TTA | AAT<br>---<br>TTA | GAC<br>---<br>CTG | AGC<br>-+-<br>TCG | AGT<br>---<br>TCA | ATT<br>---<br>TAA | CAG<br>-+-<br>GTC | TCT<br>---<br>AGA | TGC<br>---<br>ACG | TGT<br>-+-<br>ACA | TTT<br>---<br>AAA | CTA<br>---<br>GAT | GAC<br>---<br>CTG | T<br>+<br>A<br>1320 |
| 1321 | CA<br>--<br>GT | ACC<br>---<br>TGG | TAT<br>---<br>ATA | TTC<br>-+-<br>AAG | TTC<br>---<br>AAG | TGG<br>---<br>ACC | CGA<br>-+-<br>GCT | AGT<br>---<br>TCA | GGG<br>---<br>CCC | GAC<br>---<br>CTG | CTG<br>-+-<br>GAC | TTT<br>---<br>AAA | AAA<br>---<br>TTT | GTG<br>-+-<br>CAC | CCC<br>---<br>GGG | TGA<br>---<br>ACT | TCT<br>-+-<br>AGA | TTT<br>---<br>AAA | TTT<br>---<br>AAA | AGT<br>---<br>TCA | G<br>+<br>C<br>1380 |
| 1381 | TT<br>--<br>AA | GAT<br>---<br>CTA | GGC<br>---<br>CCG | TTA<br>-+-<br>AAT | TAT<br>---<br>ATA | CTT<br>---<br>GAA | ATT<br>-+-<br>TAA | ATT<br>---<br>TAA | GGG<br>---<br>CCC | CAA<br>---<br>GTT | CTG<br>-+-<br>GAC | AAG<br>---<br>TTC | ATA<br>-+-<br>TAT | TAT<br>---<br>ATA | TTA<br>---<br>AAT | ACT<br>---<br>TGA | TTT<br>-+-<br>AAA | TTC<br>---<br>AAG | TTG<br>---<br>AAC | G<br>+<br>C<br>1440 |

```
                                                    -continued
1441  CA TTT TCT ATT TTT GTT ATT ATT CTT GAC TTT GTG ATT GAG TTC ATT TTA TAC ATG AAA G
      -- --- --- -+- --- --- -+- --- --- --- -+- --- --- -+- --- --- -+- --- --- -+- -
      GT AAA AGA TAA AAA CAA TAA TAA GAA CTG AAA CAC TAA CTC AAG AAT AAT ATG TAC TTT C  1500

1501  AT ATG GAG ATG AAG AAA CAG GTT GCA AAA ATA TAT AGA GCA TTC AGA GGG CTT TGA GAC A
      -- --- --- -+- --- --- -+- --- --- --- -+- --- --- -+- --- --- -+- --- --- -+- -
      TA TAC CTC TAC TTC TTT GTC CAA CGT TTT TAT ATA TCT CGT AAG TCT CCC ACA ACT CTG T  1560

1561  AA GTC GAG AAG TGA GTT GGT TAT GCG GAT TCT TCG AGA GCA GAT CTA TAA ATC TGA TAT A
      -- --- --- -+- --- --- -+- --- --- --- -+- --- --- -+- --- --- -+- --- --- -+- -
      TT CAG CTC TTC ACT CAA CCA CGC CTA AGA AGC TCT CGT CTA GAT ATT TAG GAA ACT ACT T  1620

1621  CG TAA TTC AAA AGT ATT GGT AAT AGA CCC GAC TCA AGT TGC TAA TAT TTT TAT TTT TAA T
      -- --- --- -+- --- --- -+- --- --- --- -+- --- --- -+- --- --- -+- --- --- -+- -
      GC ATT AAG TTT TCA TAA CCA TTA TCT GGG CTG AGT TCA ACG ATT ATA AAA ATA AAA ATT A  1680

1681  CC AGA AAT AGC GCC TGC TTC TAT TTC CAT TCT AAC AAC TAA AAG TAA CTT GAA CTT GGC T
      -- --- --- -+- --- --- -+- --- --- --- -+- --- --- -+- --- --- -+- --- --- -+- -
      GG TCT TTA TCG CGG ACG AAG ATA AAG GTA AGA TTG TTG ATT TTC ACG ACG GAA CTT CCG A  1740

1741  GT CAG AAA ATA ATA AAA AGT TGA TGA AAC TAC AAC TGT TGA GCG TGA CTT GAA AGC TAG T
      -- --- --- -+- --- --- -+- --- --- --- -+- --- --- -+- --- --- -+- --- --- -+- -
      CA GTC TTT TAT TAT TTT TCA ACT ACT TTG ATG TTG ACA ACT CGC ACT GAA CTT TCG ATC A  1800

1801  AA ACT ATA AAC ACA TAC ATA AAA TAT TAT TGA ACC AGT GCG TTT TGA ACA CTT CTT AGT G
      -- --- --- -+- --- --- -+- --- --- --- -+- --- --- -+- --- --- -+- --- --- -+- -
      TT TGA TAT TTG TGT ATG TAT TTT ATA ATA ACT TGG TCA CGC AAA ACT TGT GAA GAA TCA C  1860

1861  CT ACG TCT TAT GCT TTG TGT TGA GGT GCA ATA TTT CAT TCA TTA TAT CAC CTG GAT TAT A
      -- --- --- -+- --- --- -+- --- --- --- -+- --- --- -+- --- --- -+- --- --- -+- -
      GA TGC AGA ATA CGA AAC ACA ACT CCA CGT TAT AAA AGT AGT AAT ATA GTG GAC CCT CTA G  1920

1921  TG TTA TAT GGG AGT TAA CTG TAA CCA TTT ATG TGA AAT AGG TCA AAT AAT AGA TGA AAT A
      -- --- --- -+- --- --- -+- --- --- --- -+- --- --- -+- --- --- -+- --- --- -+- -
      AC AAT ATA CCC TCA ATT GAC ATT GGT AAA TAC ACT TTA TCC AGT TTA TTA TCT ACT TTA T  1980

1981  GG AAT CTT CCA TCA TTA CTA CCA ACT TTG AGG AGG ATG TAT CTT TCC TTA TTA TTA TTA G
      -- --- --- -+- --- --- -+- --- --- --- -+- --- --- -+- --- --- -+- --- --- -+- -
      CC TTA GAA GGT AGT AAT GAT TGA AAT TCC TCC TAC ATA GAA AGG AAT AAT AAT AAT AAT C  2040

2041  CA ACA AGG ATA TTT TAA TAA TAC TCA AGA AGT GTG ATA TTT CAT CTG GTT ATG ACC TGG G
      -- --- --- -+- --- --- -+- --- --- --- -+- --- --- -+- --- --- -+- --- --- -+- -
      GT TGT TCC TAT AAA ATT ATT ATG AGT TCT TCA CAC TAT AAA GTA CAC GAC TGG TAC AGG C  2100

2101  AT AAG ACA TTT ATC GTT CTC TGG AGT TCG TAT TTT TGA TCG AAA CTG GAC ATT TAA ATT A
      -- --- --- -+- --- --- -+- --- --- --- -+- --- --- -+- --- --- -+- --- --- -+- -
      TA TTC TGT AAG TAG CAA GAG ACC TCA AGC ATA AAA ACT ACT TGT GTG CTG TAA TTT ACA T  2160

2161  AT CAT TCA TCA TAA TAA GTT GCA CTC TGA TGC TGA TTA TAT AAA TTT TGA AGA TGT AGT C
      -- --- --- -+- --- --- -+- --- --- --- -+- --- --- -+- --- --- -+- --- --- -+- -
      TA GTA AGT ATT ATT CAA CGT GAG ACT ACG ACT AAT ATA TTT AAA ACT TCT ACA TCA TCA G  2220

2221  AC AGG ATC AAT TGT AAA AGA TGT TTT TAG TGT TGT CAC GAA ATA ATA ATA TAT G
      -- --- --- -+- --- --- -+- --- --- --- -+- --- --- -+- --- --- -+- -
                                                                                       2280
```

```
                                                           -continued
       TG TCC TAG TTA ACA TCT TTT AAC AAT ACA AAA ACA ATC CTT GAC GTG ATT TAT TAT ATA C
2281   AT  |   |   |   |   |   |   |   |   |   |   |   |   |   |   |   |   |   |   | C
       TA AAG ACA GCA AAA ACG ACT GAC CAT AAT CCT TCT TTT ATT AGG AGT TGA TAA GAG AGA +     2340
          TTC TGT CGT TTT TGC TGA CTG GTA TTA GGA AGA AAA TAA TCC TCA ACT ATT CTC TCT G TA TTC ATC CTG TGT TAA AAC TCT GTT AAT TAG TAT TTT TCG TTA TGC AAA GTC TGT A
2341   AT  |   |   |   |   |   |   |   |   |   |   |   |   |   |   |   |   |   |   | +     2400
       AT AAG TAG GAC ACA ATT TTG AGA CAA TTA ATA AAA AGC AAT ACG TTT CAG ACA T AA TGA TCA TGA GAT ACT AAC CGA GAG TAA TTT ATT ATC TCA TTG CAT TTC AGA TAG T
2401   TT  |   |   |   |   |   |   |   |   |   |   |   |   |   |   |   |   |   |   | +     2460
       TT ACT AGT ACT CTA TGA TTG GCT CTC ATT TAA AAA TAG AGT AAC GTA AAG TCT ATC A AA CGG AGC TTT CTT TAA AAG TAG ATA CGT TCC CCT TAA ACG GTA CTT ACG TAA AAG GAG A
2461   TT  |   |   |   |   |   |   |   |   |   |   |   |   |   |   |   |   |   |   | +     2520
       TT GCC TCG AAA GAA TTC ATC TAT GCA AGG GGA ATT CAT GAA TGC ATT TTC CTC T AT AGC ACG AAA GAT ACC AAA TGA TTA GCA CTT TGC TAG TAA GCT T
2521   TA  |   |   |   |   |   |   |   |   |   |   |   |   |   |   |             2565
       TA TCG TGC TTT CTA TGG ACT AAT CGT GAA ACG ATC ATT CGA A
```

The following examples are provided to exemplify the means of practicing the claimed invention. These examples are not to be viewed as limiting the scope of the invention, since one or ordinary skill in the art would the art understand that equivalent methods known in the art can be used to practice the invention taught herein.

EXAMPLE 1

Filter Preparation

1. Prepare a culture of organisms from the food, environmental, or clinical samples.

2. After the desired time for colonial growth (approximately 20-24 hours growth at 37° C. on agar medium) a Whatman No. 541 filter was applied to the surface of the plate. The filter was gently pressed onto the surface of the growth to insure that all air bubbles were removed from beneath the surface of the filter and to assure that the filter was thoroughly wetted. The orientation of the filter was designated with a soft lead pencil. After the filter was allowed to remain in contact with the colonies on the agar surface for about 5-10 minutes it was removed with a smooth motion.

3. The filter was placed growth side up in a 15×100 mm petri dish over a Whatman No. 1 filter paper soaked with 3.0 ml of 0.85% saline. The filter was smoothed to assure that no air bubbles were trapped between the filters.

4. The Petri dish was covered and exposed to 650 to 700 watts of microwave irradiation for 30 seconds.

5. The Whatman No. 541 filter was transferred to another Whatman No. 1 filter soaked with 3.0 ml of lysing solution #1 (preparation described below) with forceps by gently sliding the Whatman #541 filter onto the second filter and was allowed to remain in place for 5 minutes.

6. The top filter described in section 5 above was then transferred to another Whatman No. 1 filter which had been soaked in 3.0 ml of lysing solution #2 (see below) and allowed to sit for 5 minutes.

7. Filter containing colonial material from step 6 was then transferred to a sheet of chromatography paper (an equivalent method may be used) and air dried. The filter may be stored in a vacuum desiccator at room temperature until use.

Lysing Solutions

Solution #1: 0.5M NaOH; 1.5M NaCl.
Solution #2: 1.0M Tris, pH7; 2.0M NaCl.
(See *Plasmid* 10:296-298)

EXAMPLE 2

Oligonucleotide Labelling

1. A reaction mixture is made by combining:

| | |
|---|---|
| Distilled H$_2$O | 18.8 ul |
| DNA (300 ng/reaction) | 1.7 ul |
| 10X Kinase Buffer | 2.5 ul |
| gamma-AT$^{32}$P (150 uCi; 3000 Ci/mmol) | 1.0 ul |
| T$_4$ Kinase (10 units/ul) | 1.0 ul |

2. After incubating at 37° C. for 60 minutes 4.0 ul 0.25M EDTA, pH 8 was added, followed by addition of 1.6 ul 4.0M NH$_4$OAc.

3. A NACS PREPAC column was prepared by hydrating for 1 hour using 0.25M NH$_4$OAc. The prepared mixture was then loaded on the column. Then the column was washed with 3-5 ml 0.25M NH$_4$OAc.

4. The DNA was eluted from the column using 200 ul portions of 4.0M NH$_4$OAc and the amount of radioactivity in each fraction was determined.

EXAMPLE 3

Hybridization

1. Hybridization reaction mixture was prepared by mixing the following:

| | |
|---|---|
| Distilled H$_2$O | 28.9 ml |
| 20X SSC (3.0M NaCl., 0.3M Na Citrate) | 15.0 ml |
| 50X Denhardt's Solution. (1 g. each of bovine serum albumin, focol, and polyvinylpyrrolidone in 100 ml distilled water) | 5.0 ml |
| 0.5M EDTA, pH 8.0 | 0.1 ml |

2. 1.0 ml calf thymus DNA (Mol. Wt. 300,000 to 500,000; 10 mg/ml) was boiled for 5-10 minutes, added to the hybridization reaction mixture, and stirred.

3. 8-10 ml of the hybridization mix prepared in step 2 was added to a prepared Whatman #541 filter prepared in Example 1.

4. Immediately thereafter one million cpm of DNA probe of the invention was added to the treated filter or membrane prepared in step 4 and aggitated to assure full exposure of the filter to the probe. The receptical containing the filter was then placed in an incubator at 37° C. or 18-24 hours.

EXAMPLE 4

Filter washing

1. The filter prepared above, after required incubation, was removed from the mixture, rinsed for 5-10 seconds in 6X SSC and placed in 5-10 ml of fresh 6X SSC for 60 minutes. The filter was then removed from the liquid. After addition of fresh 6X SSC, the filter in a receptical was incubated for 60 minutes.

2. Liquid was removed and the filter was washed briefly in 2X SSC, removed from solution, and allowed to air dry on chromatography paper or some equivalent surface.

EXAMPLE 5

Film Exposure

1. The dried filters were placed in an X-ray cassette with intensifying screens. (Screens were protected by covering the filters with plastic film wrap.) In a dark environment, a sheet of X-ray film was placed over the filters in the cassette, which was then exposed for 18-24 hours at −70° C.

2. After the film had warmed to room temperature, it was developed in accord with instructions provided by the film manufacturer.

The invention may also be practiced using nucleic acid isolates following known nucleic acid blotting and hybridization techniques. Examples of such techniques are discussed in Davis, et al. *Basic Methods in Molecular Biology*, New York, 1986, pp. 62-65 and 75-78. RNA blotting techniques such as Northern blotting and hybridization techniques known to those of ordinary skill in the art may also be used. See Davis, et al, (cited above) at pages 143-146 and 150-151. The above references are incorporated herein by reference. DNA may be isolated by the modified alkaline denaturation method of Birnboim and Doly, *Nucleic Acids Res.*, 7: 1513–1523 (1979), which is incorporated herein by reference.

EXAMPLE 6
RNA Isolation

1. Cells (100 ml) were grown to the end of the logarithmic phase, then centrifuged at 6000 rpm for 5 minutes. The resulting pellet was suspended in 5 ml Tris-EDTA buffer.
2. The suspension prepared in step 1 was centrifuged at 6000 rpm for 5 minutes. Cells were then resuspended in 2.5 ml Tris-EDTA.
3. To the suspension prepared in step 2, 1 ml lysozyme (0.4 mg/ml) was added. The resulting mixture was incubated 5–20 minutes at 37° C.
4. After incubation, 0.25 ml 10% sodium dodecyl sulfate was added followed by mixing. Phenol/chloroform (1:1, v/v) was added. The mixture was vortexed on ice for about 20 minutes, then centrifuged 20 minutes at 15,000 rpm.
5. The lower layer of the mixture resulting from step 4 was transferred to a sterile 30 ml beaker on ice. An equal volume of isopropanol was slowly added while spooling nucleic acid onto a glass rod.
6. Nucleic acid was dissolved in 1 ml Tris-EDTA and the phenol/chloroform extraction and isopropanol spooling was repeated. The spooled nucleic acid was then redissolved in 1 ml Tris-EDTA.
7. To the dissolved nucleic acid prepared in step 6 was added 0.1 volume 3 molar NaOAc, pH 4.5 and 2.0 volumes ethanol. The resulting mixture was placed on ice for 30 Minutes, then centrifuged at 10,000 rpm for 10 minutes. The supernatant was removed and 1.0 ml 70% ethanol was added to the residue. The resulting ethanol mixture was centrifuged as before and the supernatant removed. The residue was dried. The resulting product can be stored at −20° C. until needed.

Oligonucleotides of bases which are complementary to a specific sequence in an open reading frame of the 2.5 kilobase HindII fragment disclosed above may be used as probes by the method of the invention. However, probes of 18 to 24 bases are preferred. Probes from a variable region are preferred. For purposes of the invention, probes should have no more than 4 identical bases consecutively. Preferably, no more than two consecutive bases should be identical.

The bases complementary to the first reading frame identified have the following sequence:

ATGGACATTTCAA
GCTGGTTCGAAAGTATTCATGTGTTTTAAT

ACTCCTGAACGGCGTTTTTTTTAGATTGGCT

CCATTATTTTTCTTTCTTCCATTTTTAAATAA

CGGTATAATTTCTCCATCTATTAGAATACCTG

TGATTTTTCTTGTTGCATCAGGATTAATTACT

TCTGGTAAGGTAGACATAGGTTCTTCTGTTTT

TGAACATGTTTATTTCCTTATGTTCAAGGAAA

TAATTGTTGGCCTCCTTCTCTCTTTTTGCTTG

TCTCTTCCCTTTTGGATATTTCATGCTGTTGG

TAGCATTATTGACAACCAGCGTGGGGCAACGC

TTAGTAGTTCAATTGATCCTGCCAATGGTGTT

GATACGTCTGAGTTGGCAAAATTTTTCAATCT

TTTTTCTGCAGTTGTATTTCTATACAGTGGTG

GAATGGTCTTTATTTTAGAATCCATACAATTG

TCTTATAATATATSCCCGTTATTTTCTCAATG

TTCTTTCCGTGTCTCAAATATCTTAACATTTC

TGACTTTATTGGCAAGTCAGGCTGTTATTTTA

GCCAGTCCTGTTATGATAGTATTGTTACTATC

AGAAGTATTACTTGGTGTATTATCGAGATTGC

TCCGCAGATGA₁

Table 1 indicates that the enteroinvasive organisms were readily identified by the probe having the sequence 5'-TAATACTCCTGAACGGCG-3'.

TABLE 1
BACTERIAL STRAINS HYBRIDIZED WITH SHIGELLA PROBE

Several Shigella and enteroinvasive *E. coli* stains were hybridized against the synthetic oligonucleotide derived from the open reading frame of the 2.5 kilobase HindIII fragment. As expected, only those strains that carry the 230 kilobase pair plasmid hybridized to the probe. Other gram-negative and gram-positive bacteria tested failed to hybridize with the probe. The number in parenthesis indicates the number of strains tested.

BACTERIA TESTED BY HYBRIDIZATION WITH SHIGELLA PROBE

| Bacteria tested | Results of Hybridization | Presence of Plasmid |
|---|---|---|
| *Shigella flexneri* (4) | + | + |
| *Sh. sonnei* (1) | + | + |
| *Sh. dysentariae* (2) | + | + |
| *Sh. boydii* (1) | + | + |
| *Sh. flexneri* 354 (1) | − | − |
| *Sh. sonnei* (2) | − | − |
| *Sh. boydii* (1) | − | − |
| *Escherichia coli* (6) | + | + |
| *E. coli* (3) | − | − |
| Other gram negatives | | |
| *Enterobacter cloacae* | − | |
| *Klebsiella pneumoniae* | − | |
| *Proteus vulgaris* | − | |
| *Salmonella typhimurium* | − | |
| *Serratia marcescens* | − | |
| *Yersinia enterocolitica* (3) | − | |
| Gram positives | | |
| *Staphlycoccus aureus* | − | |
| *Staphlycoccus epidermidis* | − | |
| *Streptococcus pyogenes* | − | |
| *Streptococcus faecalis* | − | |
| *Listeria monocytogenes* | − | |
| *Listeria ivanovii* | − | |
| *Listeria seeligeri* | − | |

We claim:
1. A probe of at least 18 bases which are complementary to a specific sequence of an open reading frame of the 2.5-kilobase HindIII fragment of the sequence disclosed as:

[Sequence listing table - not transcribed in detail due to complexity]

-continued

| | | | | | | | | | | | | | | | | | | | | |
|---|---|---|---|---|---|---|---|---|---|---|---|---|---|---|---|---|---|---|---|---|
| 661 | TA<br>AT<br>eu | GCC<br>CGG<br>Ala | AGT<br>TCA<br>Ser | CCT<br>GGA<br>Pro | GTT<br>CAA<br>Val | ATG<br>TAC<br>Met | ATA<br>TAT<br>Ile | GTA<br>CAT<br>Val | TTG<br>AAC<br>Leu | TTA<br>AAT<br>Leu | CTA<br>GAT<br>Leu | TCA<br>AGT<br>Ser | GAA<br>CTT<br>Glu | GTA<br>CAT<br>Val | TTA<br>AAT<br>Leu | CTT<br>GAA<br>Leu | GGT<br>CCA<br>Gly | GTA<br>CAT<br>Val | TTA<br>AAT<br>Leu | TCG<br>AGC<br>Ser | 720 |
| 721 | GA<br>CT<br>rg | TTG<br>AAC<br>Leu | CTC<br>GAG<br>Leu | CGC<br>GCG<br>Arg | AGA<br>TCT<br>Arg | TGA<br>ACT | ATG<br>TAC | CTT<br>GAA | CCG<br>GGC | TAT<br>ATA | TAT<br>ATA | CAT<br>GTA | TAC<br>ATG | ACT<br>TGA | TGC<br>ACG | AAT<br>TTA | AAT<br>TTA | 780 |
| 781 | TT<br>AA | TAT<br>ATA | TAT<br>ATA | TTT<br>AAA | CAT<br>GTA | TTC<br>AAG | TAC<br>ATG | CTG<br>GAC | TTA<br>AAT | TAT<br>ATA | CAT<br>GTA | CTT<br>GAA | ATT<br>TAA | TTT<br>AAA | ATT<br>TAA | CCT<br>GGA | CGG<br>GCC | 840 |
| 841 | GA<br>CT | ACA<br>TGT | TAA<br>ATT | ATT<br>TAA | TTT<br>AAA | CAC<br>GTG | TGT<br>ACA | ATT<br>TAA | TGT<br>ACA | TAG<br>ATC | ATA<br>TAT | AAA<br>TTT | TAT<br>ATA | AGG<br>TCC | ACA<br>TGT | TAT<br>ATA | AAC<br>TTG | AAA<br>TTT | AGA<br>TCT | 900 |
| 901 | AA<br>TT | GCC<br>CGG | GAC<br>CTG | ACC<br>TGG | TAA<br>ATT | AAA<br>TTT | ACT<br>TGA | AAA<br>TTT | GGA<br>CCT | CGC<br>GCG | GCG<br>CGC | AAA<br>TTT | ATT<br>TAA | TAC<br>ATG | AGG<br>TCC | ACA<br>TGT | GTC<br>CAG | ATT<br>TAA | TAA<br>ATT | 960 |
| 961 | GA<br>CT | TTT<br>AAA | TGA<br>ACT | GAC<br>CTG | TGT<br>ACA | TAT<br>ATA | CTT<br>GAA | TAT<br>ATA | TGT<br>ACA | AGG<br>TCC | GAC<br>CTG | AGG<br>TCC | ATT<br>TAA | ATC<br>TAG | CGA<br>GCT | AAT<br>TTA | ATT<br>TAA | 1020 |
| 1021 | TT<br>AA | CTG<br>GAC | TGT<br>ACA | TCT<br>AGA | AAT<br>TTA | GCT<br>CGA | CTT<br>GAA | CAG<br>GTC | TAT<br>ATA | TGT<br>ACA | AAC<br>TTG | ATT<br>TAA | AAA<br>TTT | TCA<br>AGT | CAG<br>GTC | AAT<br>TTA | GTT<br>CAA | CTT<br>GAA | TGG<br>ACC | AAA<br>TTT | 1080 |
| 1081 | GG<br>CC | TAA<br>ATT | ATA<br>TAT | CTT<br>GAA | ACC<br>TGG | TGC<br>ACG | TAT<br>ATA | GCC<br>CGG | GTT<br>CAA | ATT<br>TAA | CTT<br>GAA | AAT<br>TTA | TTT<br>AAA | GGT<br>CCA | ATT<br>TAA | GAT<br>CTA | CTT<br>GAA | TGT<br>ACA | CCC<br>GGG | CTT<br>GAA | 1140 |
| 1141 | TT<br>AA | CTG<br>GAC | TGT<br>ACA | TCT<br>AGA | TTC<br>AAG | AAT<br>TTA | GGC<br>CCG | CCC<br>GGG | AAC<br>TTG | ATT<br>TAA | TCA<br>AGT | AAT<br>TTA | AAA<br>TTT | CCA<br>GGT | ATC<br>TAG | AAT<br>TTA | CTT<br>GAA | TGC<br>ACG | GAC<br>CTG | 1200 |
| 1201 | AA<br>TT | AGC<br>TCG | TAT<br>ATA | TCT<br>AGA | TGT<br>ACA | CAA<br>GTT | ATT<br>TAA | GTT<br>CAA | TTT<br>AAA | AGA<br>TCT | GAT<br>CTA | ATT<br>TAA | AAA<br>TTT | TCT<br>AGA | AGG<br>TCC | CTT<br>GAA | AAA<br>TTT | AAT<br>TTA | AAA<br>TTT | TGA<br>ACT | 1260 |
| 1261 | AG<br>TC | TAT<br>ATA | AAA<br>TTT | GAC<br>CTG | AAT<br>TTA | ATT<br>TAA | TTT<br>AAA | CAA<br>GTT | GAT<br>CTA | AGC<br>TCG | CGA<br>GCT | AAA<br>TTT | AGA<br>TCT | AAT<br>TTA | CTT<br>GAA | TTT<br>AAA | CTA<br>GAT | TTT<br>AAA | CTA<br>GCA | TTT<br>AAA | 1320 |
| 1321 | CA<br>GT | ACC<br>TGG | TAT<br>ATA | TTC<br>AAG | AAA<br>TTT | TGG<br>ACC | GGG<br>CCC | CGA<br>GCT | CTG<br>GAC | CAG<br>GTC | CAG<br>GTC | CAC<br>GTG | GTG<br>CAC | TCA<br>AGT | TCT<br>AGA | TTT<br>AAA | AGT<br>TCA | 1380 |
| 1381 | TT<br>AA | GAT<br>CTA | GGC<br>CCG | TTA<br>AAT | TAT<br>ATA | ATT<br>TAA | CTT<br>GAA | GAA<br>CTT | CTG<br>GAC | GGG<br>CCC | CCC<br>GGG | CTG<br>GAC | TTT<br>AAA | GAT<br>CTA | TTA<br>AAT | TTT<br>AAA | ATT<br>TAA | TTC<br>AAG | ATT<br>TAA | TTG<br>AAC | 1440 |

-continued

```
     CA TTT TCT ATT TTT GTT ATT ATT CTT GAC TTT GTG ATT GAG TTC ATT TTA TAC ATG AAA G
1441 -- --- --- -+- --- --- --+ --- --- --- +-- --- --- -+- --- --- --+ --- --- --- + 1500
     GT AAA AGA TAA AAA CAA TAA TAA GAA CTG AAA CAC TAA CTC AAG TAA AAT ATG TAC TTT C

AT ATG ATG ATG GAT AAA CAG GAG ATA AAA ATA TAT AGA GCA AGA GGG ACA CTT TGA GAC A
1501 -- --- --- -+- --- --- --+ --- --- --- +-- --- --- -+- --- --- --+ --- --- --- + 1560
     TA TAC TAC TAC CTA TTT GTC CTC TAT TTT TAT ATA TCT CGT TCT CCC TGT GAA ACT CTG T

AA GTC GAG AAG GCG TGA GTT GCA TAT CGA GAT TCT TTC AGA GCA GAC TAA ATC TGA TAT A
1561 -- --- --- -+- --- --- --+ --- --- --- +-- --- --- -+- --- --- --+ --- --- --- + 1620
     TT CAG CTC TTC CGC ACT CAA CGT ATA GCT CTA AGA AAG TCT CGT CTG ATT TAG ACT ATA T

CG TAA TTC AAA ATT AGT GGT AAT GAA CCC GAC TCA TAT TGC AAT TGG TAT TTA TTT TAA T
1621 -- --- --- -+- --- --- --+ --- --- --- +-- --- --- -+- --- --- --+ --- --- --- + 1680
     GC ATT AAG TTT TAA TCA CCA TTA CTT GGG CTG AGT ATA ACG TTA ACC ATA AAT AAA ATT A

CC AGA AAT AGC GCC TGC ACC TTT TAT TTC TCT CAT TGA AAC TAA CCA GTG TGC CTT GGC T
1681 -- --- --- -+- --- --- --+ --- --- --- +-- --- --- -+- --- --- --+ --- --- --- + 1740
     GG TCT TTA TCG CGG ACG TGG AAA ATA AAG AGA GTA ACT TTG ATT GGT CAC ACG GAA CCG A

GT CAG AAA ATA TGC AAA TGA AGT TGG TAT ACC AAC TGT GCG TGA TGT GAA ATT AGC TAG A
1741 -- --- --- -+- --- --- --+ --- --- --- +-- --- --- -+- --- --- --+ --- --- --- + 1800
     CA GTC TTT TAT ACG TTT ACT TCA ACC ATA TGG TTG ACA CGC ACT ACA CTT TAA TCG ATC T

AA ACT ATA TAA AAC ACA TAC AAA ATA TAG TTT TGT TGA TTT TGA ACA CTT GGA TGA AGT C
1801 -- --- --- -+- --- --- --+ --- --- --- +-- --- --- -+- --- --- --+ --- --- --- + 1860
     TT TGA TAT ATT TTG TGT ATG TTT TAT ATC AAA ACA ACT AAA ACT TGT GAA CCT ACT TCA G

CT ACG TCT TAT TGT TTG GCT TGA GCA GGT TGA AAA CAC TCA TTA ATA AGT AAA GGA GAT G
1861 -- --- --- -+- --- --- --+ --- --- --- +-- --- --- -+- --- --- --+ --- --- --- + 1920
     GA TGC AGA ATA ACA AAC CGA ACT CGT CCA ACT TTT GTG AGT AAT TAT TCA TTT CCT CTA C

TG TTA TAT GGG AGT TAA TTT CTG TAA TAA AAT AGG TAT TGA TCA GTC TGA ATT TGA AAT A
1921 -- --- --- -+- --- --- --+ --- --- --- +-- --- --- -+- --- --- --+ --- --- --- + 1980
     AC AAT ATA CCC TCA ATT AAA GAC ATT ATT TTA TCC ATA ACT AGT CAG ACT TAA ACT TTA T

GG AAT CTT CCA TCA TTA ACT CCA TTG CTA ATG AGG TAT TGA ACC CAA TAT CTT TCC TTA G
1981 -- --- --- -+- --- --- --+ --- --- --- +-- --- --- -+- --- --- --+ --- --- --- + 2040
     CC TTA GAA GGT AGT AAT TGA GGT AAC GAT TAC TCC ATA ACT TGG GTT ATA GAA AGG AAT C

CA ACA AGG ATA TAA TAA ATG TTT TAC TCA GAA AGA TTT CAT CTG AAT GTG ACC TGG TTA G
2041 -- --- --- -+- --- --- --+ --- --- --- +-- --- --- -+- --- --- --+ --- --- --- + 2100
     GT TGT TCC TAT ATT ATT TAC AAA ATG AGT CTT TCT AAA GTA GAC TTA CAC TGG ACC AAT C

AA AAG ACA TTT ATC GTT GTG CTC TGG AGT TGG TCG TTG AAA AAA CAC CTG ATG ATT TAT A
2101 -- --- --- -+- --- --- --+ --- --- --- +-- --- --- -+- --- --- --+ --- --- --- + 2160
     TT TTC TGT AAA TAG CAA CAC GAG ACC TCA ACC AGC AAC TTT TTT GTG GAC TAC TAA ATA T

AT CAT TCA TAA TAA CTC TTT TGC TGA TAT AAA TAT TTT TGT TGA AGA TAT TTA TGT AGT C
2161 -- --- --- -+- --- --- --+ --- --- --- +-- --- --- -+- --- --- --+ --- --- --- + 2220
     TA GTA AGT ATT ATT GAG AAA ACG ACT ATA TTT ATA AAA ACA ACT TCT ATA AAT ACA TCA G

AC AGG ATC AAT TGT AGA AAA TTG TTA TGT TTT TGT TAG GAA CTG CAC TAA ATA ATA TAT G
2221 -- --- --- -+- --- --- --+ --- --- --- +-- --- --- -+- --- --- --+ --- --- --- + 2280
```

```
              TG TCC TAG TTA ACA TCT TTT AAC AAT ACA AAA ACA ATC CTT GAC GTG ATT TAT TAT ATA C
2281    AT    AAG ACA GCA TGT ACG ACT GAC CAT AAT CCT TCT TTT ATT AGG AGT TGA TAA GAG AGA C  2340
        TA    TTC TGT CGT ACA TGC TGA CTG GTA TTA AGA AAA TAA ACT TCC TCA ATT CTC TCT G

2341    TA    TTC ATC CTG TAA TGT AAC TAA TCT GTT GAC CAT TAT TTT TCG CGA TTA AAA GTC TGT A  2400
        AT    AAG TAG GAC ATT ACA ATT TTG AGA CAA ATA ATA AAA AGC AAT ACG TTT CAG ACA T

2401    AA    TGA TCA TGA GAT ACT AAC CGA GAG TAA TTT ATT TCG ATC TCA TTG CAT AGA TAG T  2460
        TT    ACT AGT ACT CTA TGA TTG GCT CTC ATT AAA AGC TAG AAC GTA TCT ATC A

2461    AA    CGG AGC TTT CTT TAA AAG TAG ATA TCC CGT TAA GTA CTT ACG AAG GAG A  2520
        TT    GCC TCG AAA GAA ATT TTC ATC TAT AGG GCA ATT CAT GAA TGC TTC CTC T

2521    AT    AGC ACG AAA GAT ACC AAA TGA TTA GCA CTT TAG TAA GCT T  2565
        TA    TCG TGC TTT CTA TGG ACT AAT CGT GAA AAT ATC CGA A
```

2. A probe comprising at least 18 consecutive bases of the sequence

```
                        ATGGACATTTCAA
GCTGGTTCGAAAGTATTCATGTGTTTTTAAT
ACTCCTGAACGGCGTTTTTTTTAGATTGGCT
CCATTATTTTTCTTTCTTCCATTTTTAAATAA
CGGTATAATTTCTCCATCTATTAGAATACCTG
TGATTTTTCTTGTTGCATCAGGATTAATTACT
TCTGGTAAGGTAGACATAGGTTCTTCTGTTTT
TGAACATGTTTATTTCCTTATGTTCAAGGAAA
TAATTGTTGGCCTCCTTCTCTCTTTTTGCTTG
TCTCTTCCCTTTTGGATATTTCATGCTGTTGG
TAGCATTATTGACAACCAGCGTGGGGCAACGC
TTAGTAGTTCAATTGATCCTGCCAATGGTGTT
GATACGTCTGAGTTGGCAAAATTTTTCAATCT
TTTTTCTGCAGTTGTATTTCTATACAGTGGTG
GAATGGTCTTTATTTTAGAATCCATACAATTG
TCTTATAATATATSCCCGTTATTTTCTCAATG
TTCTTTCCGTGTCTCAAATATCTTAACATTTC
TGACTTTATTGGCAAGTCAGGCTGTTATTTTA
GCCAGTCCTGTTATGATAGTATTGTTACTATC
AGAAGTATTACTTGGTGTATTATCGAGATTGC
TCCGCAGATGA₁
``` with the proviso that no more than 4 consecutive bases are identical.

3. A probe of claim 2 wherein no more than 2 consecutive bases are identical.

4. A probe of claim 2 which has 18 to 24 bases.

5. A probe of claim, 2 which has the sequence:

5'-TAATACTCCTGAACGGCG-3'

6. A method of identifying enteroinvasive Shigellae species or *E. coli* comprising the steps of:
  (1) culturing an isolate suspected of containing an enteroinvasive *E. coli* or Shigellae species;
  (2) preparing a lysate of the organisms;
  (3) exposing the lysate product from step (2) to a probe of claim 2; and
  (4) inspecting the product obtained in step (3) for evidence of hybridization.

7. A method of identifying enteroinvasive Shigellae species or *E. coli* comprising the steps of:
  (1) preparing a nucleic acid isolate from a culture of Shigellae species or *E. coli* grown from a food, environmental or clinical sample;
  (2) exposing the isolate prepared in step (1) to a probe of claim 2 under hybridizing conditions; and
  (3) inspecting the sample obtained in step (2) for presence of hybridization.

8. A method of claim 6 wherein the probe has the sequence:

5'-TAATACTCCTGAACGGCG-3'.

9. A method of claim 7 wherein the probe has the sequence:

5'-TAATACTCCTGAACGGCG-3'.

* * * * *